United States Patent
Dujardin et al.

(10) Patent No.: US 8,614,088 B2
(45) Date of Patent: Dec. 24, 2013

(54) SYSTEM AND METHOD FOR LARGE-SCALE INFILTRATION OF PLANTS

(75) Inventors: Ralf Dujardin, Duesseldorf (DE);
Sebastian Schmidt, Haan (DE);
Markus Zamponi, Leverkusen (DE)

(73) Assignee: Bayer Innovation GmbH, Halle (DE)

( * ) Notice: Subject to any disclaimer, the term of this patent is extended or adjusted under 35 U.S.C. 154(b) by 436 days.

(21) Appl. No.: 12/863,933

(22) PCT Filed: Jan. 23, 2009

(86) PCT No.: PCT/EP2009/000412
§ 371 (c)(1),
(2), (4) Date: Jul. 21, 2010

(87) PCT Pub. No.: WO2009/095183
PCT Pub. Date: Aug. 6, 2009

(65) Prior Publication Data
US 2010/0299785 A1    Nov. 25, 2010

(30) Foreign Application Priority Data
Feb. 1, 2008 (EP) .................................... 08001863

(51) Int. Cl.
*C12M 1/00* (2006.01)
*C12M 3/00* (2006.01)

(52) U.S. Cl.
USPC ........................................ 435/285.1; 47/62 E (58) Field of Classification Search
USPC ................. 435/285.1, 290.1–290.4; 414/217; 47/62 E, 1.4; 800/278
See application file for complete search history.

(56) References Cited

U.S. PATENT DOCUMENTS

| | | | |
|---|---|---|---|
| 2004/0060491 A1* | 4/2004 | Leduc et al. | 111/105 |
| 2004/0088918 A1 | 5/2004 | Craig et al. | |
| 2004/0118729 A1 | 6/2004 | Craig et al. | |
| 2005/0039396 A1 | 2/2005 | Marchildon | |
| 2005/0226794 A1* | 10/2005 | Hodge et al. | 422/243 |
| 2005/0246786 A1 | 11/2005 | Adams et al. | |
| 2006/0021929 A1* | 2/2006 | Mannheim et al. | 210/321.6 |

FOREIGN PATENT DOCUMENTS

| | | |
|---|---|---|
| EP | 1 616 959 | 1/2006 |
| WO | 01/12828 | 2/2001 |
| WO | 2005/015977 | 2/2005 |

OTHER PUBLICATIONS

European Search Report of EP 08 00 1863, dated Jul. 10, 2008 (5 pages).
Clough et al., "Floral dip: a simplified method for Agrobacterium-mediated transformation of Arabidopsis thaliana," The Plant Journal, 1998, pp. 735-743, 16(6), Blackwell Science Ltd.
Bayerisches Landesamt fuer Wasserwirtschaft, Merkblatt Nr. 3.3/3 from Mar. 21, 1995.
International Search Report of PCT/EP2009/000412 dated Mar. 16, 2009 (2 pages).

\* cited by examiner

*Primary Examiner* — Michael Hobbs
(74) *Attorney, Agent, or Firm* — Miles & Stockbridge, P.C.

(57) ABSTRACT

The present invention relates to a system and method for the infiltration of plants in a continuous or quasi-continuous operation mode. The system and method of the present invention combine mechanical (automatic and manual) movable and manipulable units and/or containers with vacuum infiltration chambers to enable large-scale infiltration of plants.

11 Claims, 10 Drawing Sheets

SYSTEM AND METHOD FOR LARGE-SCALE INFILTRATION OF PLANTS

CROSS REFERENCE TO RELATED APPLICATIONS

This application is a §371 National Stage Application of PCT/EP2009/000412 filed Jan. 23, 2009, which claims priority to European Application 08001863.3 filed Feb. 1, 2008.

BACKGROUND OF THE INVENTION

1. Field of the Invention

The present invention relates to a system and method for the infiltration of plants in a continuous or quasi-continuous operation mode. The system and method of the present invention combine mechanical (automatic and manual) movable and manipulable units and/or containers with vacuum infiltration chambers to enable large-scale infiltration of plants.

2. Description of Related Art

Genetic transformation of higher plants promises to have a major impact on large-scale production of proteins of industrial importance. Various methods are known to modify plants by genetic transformation. One approach to produce foreign proteins in plants is to generate stable transgenic plant lines. A faster alternative method is based upon transient transformation by contacting the surface of a plant with a suspension of infectious particles such as a virus and/or microorganisms such as *agrobacterium tumefaciens*. By the infiltration of the infectious particles and/or microorganisms, the genetic information is transiently introduced into the cell.

The infiltration can for example be realized by using the magnICON™ technology [EP1616959]. Here, the plants, growing in solid substrate, are dipped upside down in a suspension of agrobacteria in buffer. In this state a vacuum is drawn leading to a degasification of the plants capillaries (predominantly in the leafs). After the vacuum is reached, it is released rapidly so that agrobacteria suspension is drawn into the plants capillaries. The agrobacteria can now infect the plant cells very efficiently leading to a transient genetic modification of the plant. The plant is taken out of the suspension; turned again upside up and brought to the incubation area. Here, the modified plant cells are producing the specific protein. After incubation the plants are harvested and the protein is purified. However, this method has so far only been conducted on a laboratory scale.

Conventional devices for carrying out the vacuum infiltration method are for example box type chambers with a top lid. The box is filled with an agrobacteria suspension and the plants are placed upside down. The lid is closed and the vacuum is drawn. Beneficial in this approach is predominantly the nearly optimal usage of space. On the other hand the open handling of the plants after the dipping process is likely to cause spilling not only on the vacuum chamber itself, but also on the handling unit and the room. As the agrobacteria suspension contains genetically modified organisms (GMO's), spilling has to be avoided. If spills can not be prevented, the device should at least be easy cleanable. Both problems are not addressed by conventional box type vacuum chambers.

Another issue with such conventional devices is scalability. The dimensions of a conventional box type chamber are illustratively in width: 1-2 m; length: 1-2 m; and height: 1-2 m. For a very large dipper unit, a massive and expensive scale-up by numbering would be necessary.

Infiltration of plants with or without vacuum is a known bench-scale method [see e.g. Clough et al., The Plant Journal (1998) 16(6), 735-743]. The method is normally performed with entire plants. Sometimes only some parts of the plant are cut off and processed (such as e.g. a leaf). In either case, the manipulation of plants or part of plants are carried out by hand.

In chemistry, exsiccators/drying chambers or small vacuum chambers are normally used as vacuum chambers. These are either directly filled with a liquid comprising GMO's or poured into a cartridge (inliner).

A large-scale use of vacuum chambers for plant infiltration is not known. A plant manipulation method which uses vacuum chambers is the boiler-vacuum-pressure method (full pressure method) for the impregnation of wood [e.g. Bayerisches Landesamt für Wasserwirtschaft, Merkblatt Nr. 3.3/3 from Mar. 21, 1995]. With this method, stacked wood is transferred batchwise into a vacuum chamber. The vacuum chamber is closed; vacuum is drawn and the chamber is flooded with an impregnation agent. After vacuum is removed, the impregnation agent infiltrates the wood and the remaining impregnation agent is drained. Then, the vacuum chamber can be opened again.

Due to various reasons this method is not commensurate with the solution provided by the present invention. Flooding of the chamber cannot be realized with liquid comprising GMO's as the chamber can be contaminated and the environment can be polluted after the chamber is opened. In addition, with this method the plant substrate would be soaked with liquid comprising GMO's. However, due to hygienic reasons and the fact that an unproportional high amount of liquid comprising GMO's would be lost, this has to be avoided. Furthermore, the solution provided by the present invention requires applying the vacuum after dipping of the plants. The described boiler-vacuum pressure method does not allow such a chronological order.

A further difference to the boiler-vacuum-pressure method results from the low throughput per batch due to the fact that plants—in contrast to wood—are to sensitive for stacking. The boiler-vacuum pressure method is also not suited as the process time for one batch is several hours. Such a high residence time is adverse for a high-through put approach. The solution provided by the present invention allows infiltration of plants in a continuous or quasi-continuous operation mode with cycle times of 20 minutes or lower. A technical operation mode with more than one unit in a continuous or semi-continuous way was not known in the prior art.

SUMMARY OF THE INVENTION

The technical problem of the present invention was therefore to provide a scalable solution for high-throughput infiltration of plants. Besides enabling high capacity, the solution shall also allow automatization in a continuous or quasi-continuous operation mode. In addition, the solution has to comply with the biological safety requirements for production systems that use GMO's.

The technical problem is solved by a system for the infiltration of a suspension of infectious particles and/or microorganisms (5) into at least one plant (3) comprising:
   a) at least one enclosed chamber (1) comprising:
      at least one closable opening (2) through which the at least one plant (3) in at least one container (4) is transported into and out of the at least one enclosed chamber (1) by loading and unloading means,
      a vacuum providing means for applying a vacuum to said chamber, and
   b) loading and unloading means comprising a technical transportation system to transport the at least one plant (3) in at least one container (4) into and out of the at least one enclosed chamber (1), and c) means by which at least one part of the at least one plant (3) is contacted with a suspension of infectious particles and/or microorganisms (5).

DETAILED DESCRIPTION OF A PREFERRED EMBODIMENT

The present invention provides a system for the infiltration of a suspension of infectious particles and/or microorganisms (5). The term "infectious particles" according to the present invention means viruses, viroids, virusoids and the like. The term "microorganisms" means bacteria, fungi, algae and the like. Particularly preferred is a suspension of agrobacteria *tumefaciens*. Even more preferred is a suspension of genetically engineered agrobacteria *tumefaciens*. The skilled person in the art is familiar with the infectious particles and/or microorganisms that can be infiltrated into plants with the present system and method.

As used herein, the term "plant" includes whole plants or parts of plants. Particularly preferred are whole plants. For the infiltration system of the present invention all kind of plants can be used. However, in a preferred embodiment of the invention tobacco plants are used. Even more preferred is the use of *Nicotiana benthamiana* plants.

The present invention comprises at least one enclosed chamber (1). The at least one enclosed (infiltration) chamber (1) serves to accomplish the infiltration within an enclosed box. This is advantageous and—owing to circumstances prescribed by law (biological safety)—even necessary when particulate material or other pollution is generated by liquids comprising GMO's.

In a preferred embodiment of the invention, an autoclave is used as an enclosed chamber (1). Commercially available autoclaves already combine two functions that are required or beneficial for the present invention, they can draw vacuum and they can sterilize itself to inactivate spills. Therefore, an autoclave provides vacuum providing and disinfection means. By using commercially available autoclaves, the production costs for the infiltration system of this invention can therefore be reduced.

In one embodiment of the invention cylindrical autoclaves are used as enclosed infiltration chambers (1). In an alternative embodiment, cubical autoclaves are also deployable. Depending on the concrete case, either type might be chosen for large-scale infiltration of plants.

In the preferred embodiment of the invention the at least one container (4) is at least one tray holding the at least one plant (3), which is embedded in a substrate. The tray (4) and substrate hold the plant (3) so as to allow upside down turning of the tray (and plant). In addition, the tray (4) may comprise means to avoid falling off the substrate during the rotation process. These means can be for example grids, films, filter, canvas and the like. Trays (4) are preferable subdivided in cells, which allow the production of more plants of uniform size in a smaller area. The cells of the trays (4) can be filled either with soil or a soilless medium, e.g. peat, vermiculite, rockwool, polymeric fibers, cellulosic fibers or mixtures thereof. The cells in the trays (4) can be perforated in the bottom to allow water and nutrient uptake.

As an alternative, at least the roots of the plant (3) are dipped into a liquid culture medium (4). In this embodiment, the container (4) is constructed as a floating tray. The stem of the plant (3) goes through a hole of a e.g. polystyrene, polypropylene, styrofoam or cardboard plate. The floating tray (4) is capable of immobilizing the plant(s) on the plate(s).

In the preferred embodiment of the invention the containers (4) are made from light weight materials, e.g. polystyrene, polypropylene, styrofoam or cardboard to reduce the load for the transportation system.

A pure continuous operation can be realized by an automatic separation of the enclosed infiltration chamber (1) from the loading and unloading area. For this, closable opening(s) (2a; 2b), preferably electronically closable opening(s), are used that can be clocked to the loading and unloading velocity.

In a preferred embodiment of the invention, there is one closable opening (2a) through which the at least one plant (1) in at least one container (4) is transported into and out of the at least one enclosed chamber (1) by loading and unloading means. In an even more preferred embodiment of the invention, loading and unloading occurs independently from each other with at least two closable openings (2a; 2b).

The infiltration system of the present invention further comprises vacuum providing means for applying a vacuum to the enclosed chamber (1). For the purpose of the present invention, it is preferably required to draw a vacuum of about 10 to about 300 mbar absolute, preferably about 50 to about 150 mbar absolute. The time for drawing a vacuum can be as minimal as possible or longer. For achieving a high turnover, a drawing time below 30 min is preferred, a drawing time below 10 min is particularly preferred.

Vacuum providing means are known to the skilled person in the art. As discussed above, the use of an autoclave is preferred as the vacuum that can be drawn from such a device is sufficient to infiltrate plants with infectious particles and/or microorganisms.

In a preferred embodiment of the invention, the vacuum providing means do further comprise a sterile filter to avoid that air exhaust (e.g. aerosols comprising suspension of infectious particles and/or microorganisms) leaks from the vacuum providing means.

The present system also comprises loading and unloading means comprising a technical transportation system to transport the at least one plant (3) in the at least one container (4) into and out of the at least one enclosed chamber (1).

The automatic movement of plant material on a tray or in a pot is known in the prior art in the horizontal direction. Pots and trays can be placed on transportation means for packaging reasons.

US 2004/0118729 discusses turning of plants in the vertical axis.

US 2005/0039396 relates to a rotary hydroponic plant-growing machine comprising a cylindrical structure for holding plant-growing containers, a base for rotatably supporting the cylindrical structure, means for rotating the cylindrical structure on the base, a light inside the cylindrical structure and means for watering the plants in the containers as the cylindrical structure rotates. In this application, the plants are positioned in the cylindrical structure whereas the substrate is accessible to a reservoir comprising water and other plant nutrients outside the cylindrical structure. Therefore, this machine can solely be used for plant watering. By rotating the cylindrical structure all plants can be watered one after another. The objective of US 2005/0039396 is to guarantee a regular watering of all plants by a continuous and very slow rotation of the cylindrical structure. At the same time, all plants are homogenously exposed to light by the lamp inside the cylindrical structure.

A device according to US 2005/0039396 is not suitable for the purpose of the current invention. At first, plants are dipped into a solution with the substrate causing loss and spilling. Further, the loading density of the solution according to US 2005/0039396 is not suitable for large-scale applications. The delivery rate of the provided solution increases with the outer surface of the cylindrical structure. The required space of the vacuum chamber, however, is determined by the volume of the cylindrical structure. This is a classical scaling problem. In addition, the core of the cylindrical structure remains unused and the lamp inside the cylindrical structure is not required for the purposes of the present invention.

Therefore, the present invention addresses different transportation problems and comprises different loading an unloading means.

The technical transportation system of the present invention comprise mechanic and/or electronic rail systems, manually and/or electronically movable cart systems, manually movable and/or motorized chain block systems and/or other mechanical, electrical, hydraulic, pneumatic and/or robotic transportation systems. Preferred are mechanic and/or electronic rail systems optionally comprising at least one robot handling unit and/or manually and/or electronically movable cart systems optionally comprising at least one robot handling unit.

A even more preferred embodiment of the invention relates to a system, wherein the technical transportation system comprises at least one mechanic and/or electric rail system and optionally at least one robot handling unit (20) to transport the at least one plant (3) on the at least one container (4) into and out of the at least one enclosed chamber (1).

Another preferred embodiment of the invention comprises a system, wherein the at least one mechanic and/or electric rail system comprises at least one rail (6a) and at least one carriage or suspension trolley (6b) to transport the at least one container (4) into and out of the at least one enclosed chamber (1), wherein the at least one carriage or suspension trolley (6b) is mounted within the at least one rail with at least one coupling (13).

A further preferred embodiment of the invention relates to a system, wherein the at least one carriage or suspension trolley (6b) further comprises:

means (11) by which the at least one container (4) is reversibly affixed to, and means (12) by which the at least one container (4) is reversibly turned upside down.

Mechanic and/or electric rail and monorail systems are established technologies for material transport. They allow a high degree of automation while keeping the complexity limited. However, they are not know in the context of the present invention.

Mechanic and/or electric rail system according to the present invention have to be interpreted as to include systems where the carriage or suspension trolley (6b) is moved manually by a mechanic system or electrically e.g. by a motorized system. The present invention also comprises combinations of mechanic and electric systems.

In a preferred embodiment of the invention the containers (4) are handled individually. They are turned and moved into the at least one enclosed chamber (1). In a further preferred embodiment, the containers (1) are rotated before or, during or after the loading process upside down. Inside the chamber (1) the suspension (5)—preferably within an open basin (8)—is brought together with the plants (3). The vacuum cycle is performed and the containers (4) are again moved out of the enclosed chamber (1). The turning of the containers (4) may either be done inside the vacuum chamber (1) or in a separate subsequent wet area. In a preferred embodiment of the invention, the containers (4) are rotated to their original position before they are unloaded from the enclosed vacuum chamber to avoid and/or minimize spilling. In such a system, the drops remain inside the enclosed vacuum chamber (1) and can be easily removed and—when an autoclave is used—directly inactivated.

Figure 9A:
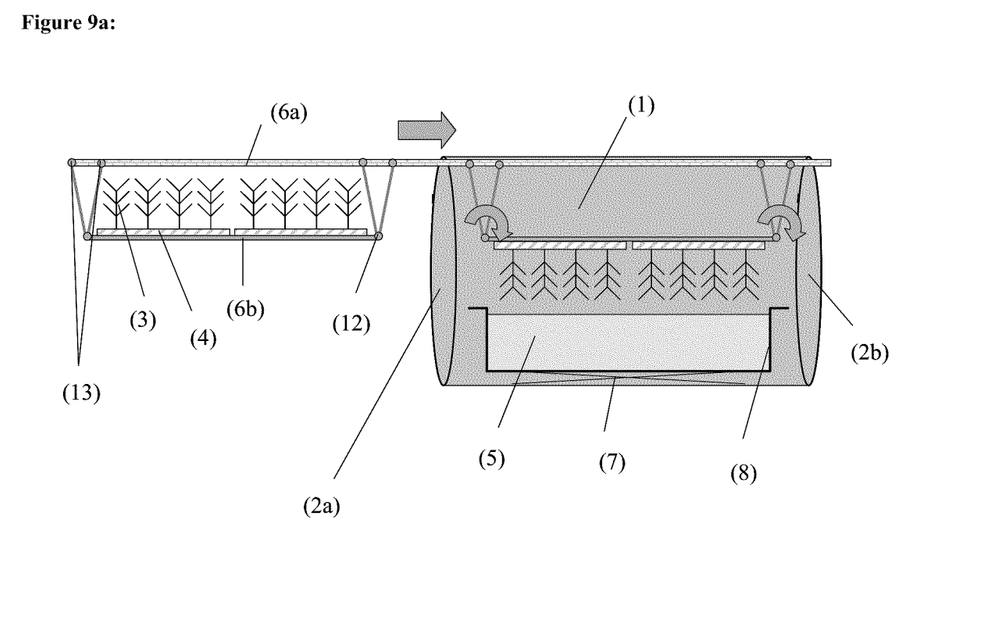
FIGS. 9a and 9b: Another example of an mechanic and/or electric rail system. This system is particularly qualified to be operated manually.
Figure 9B:
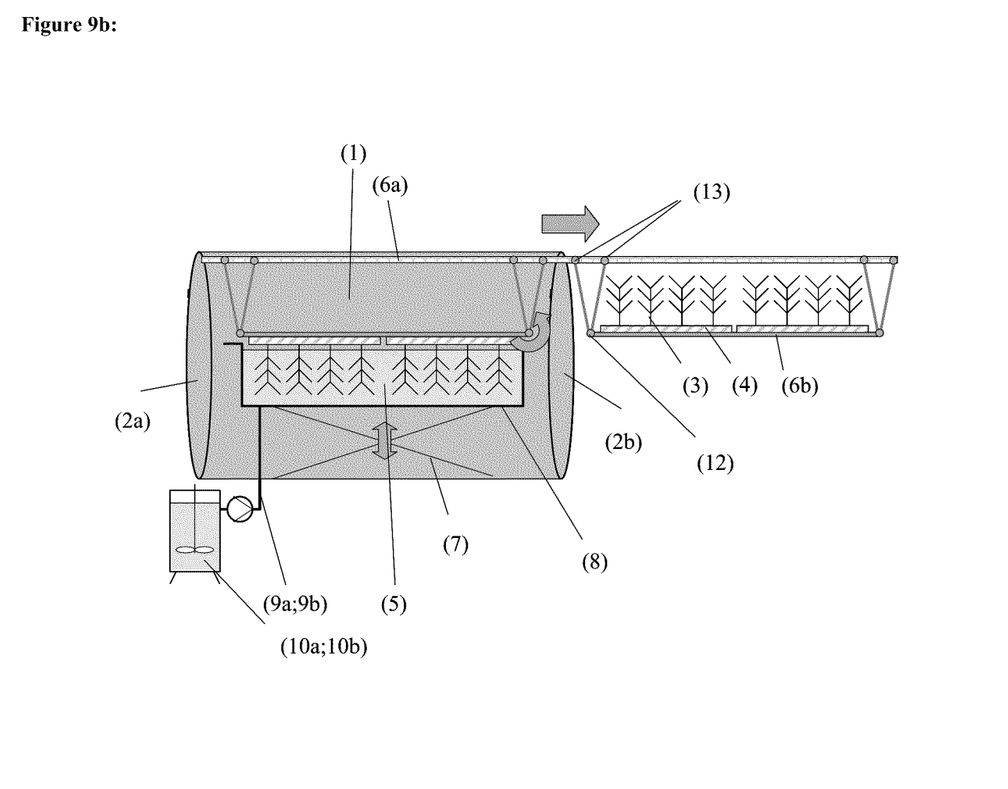

The transportation means (6a; 6b) for transporting the at least one container (4) into and out of the at least one enclosed chamber (1) comprise at least one rail (6a) and at least one carriage or suspension trolley (6b) that is mounted within the rail (6a) with at least one coupling (13). In a preferred embodiment, one carriage or suspension trolley (4) has the dimensions to fit into the enclosed chamber (1) in such a way that only one carriage or suspension trolley has to be transported into the enclosed chamber (1) to entirely fill the chamber with the plants (3; see FIG. 9a, 9b). A preferred transportation means is a monorail system. In another preferred embodiment of the invention the rail system builds an enclosed cycle. The carriage or suspension trolley (6b) preferably travels by at least one wheel (which is/are part of the coupling (13)) and is for example powered by an engine that is remote-controlled by a computer system. In another embodiment of the invention the electric monorail system is a magnetic suspension railway. The skilled person in the art is aware of other applicable transportation means to move the carriage or suspension trolley (6b) with the rail (6a) system including manual systems. The skilled person is also familiar with different couplings (13) that are useful for the present invention.

Figure 6:
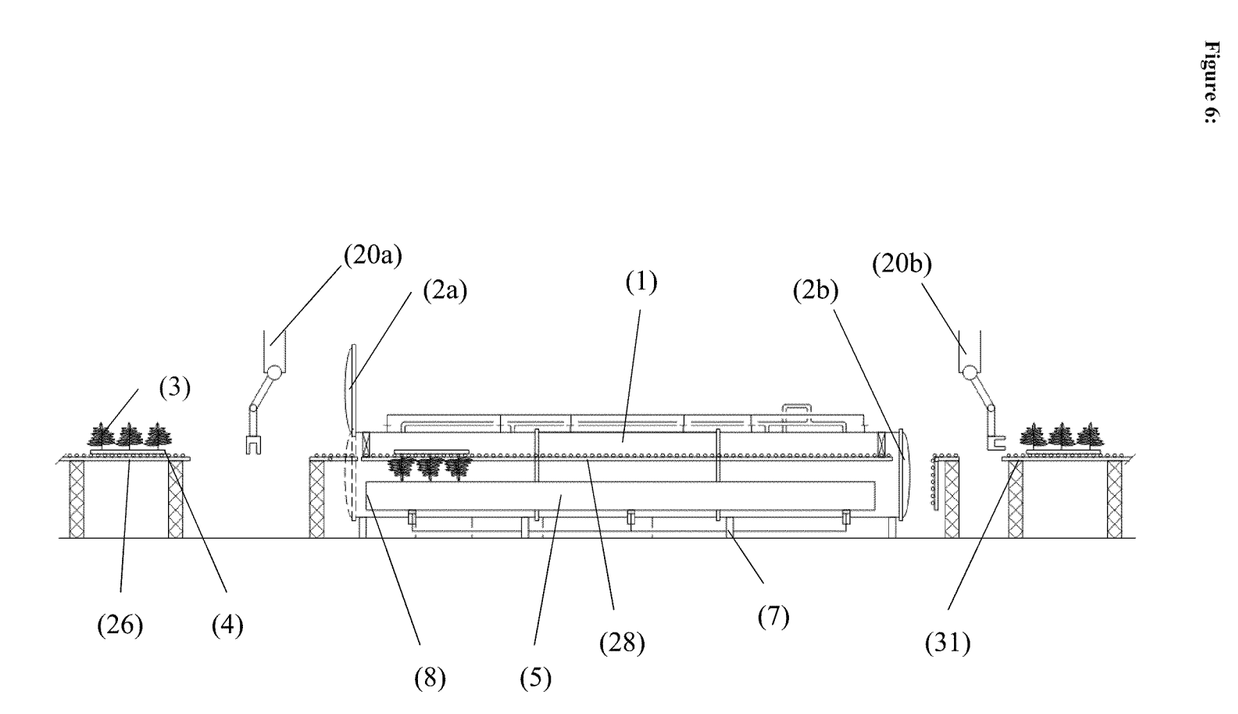
FIG. 6: Another side view of the infiltration system with at least two robot handling units (20).

The transportation means are constructed to allow opening and closing of the enclosed chamber (1) by the at least one closable opening (2a). The rail (6a) can therefore be easily dis-/reconnected to allow opening/closing of the enclosed chamber (1; see for example FIG. 6).

Figure 10:
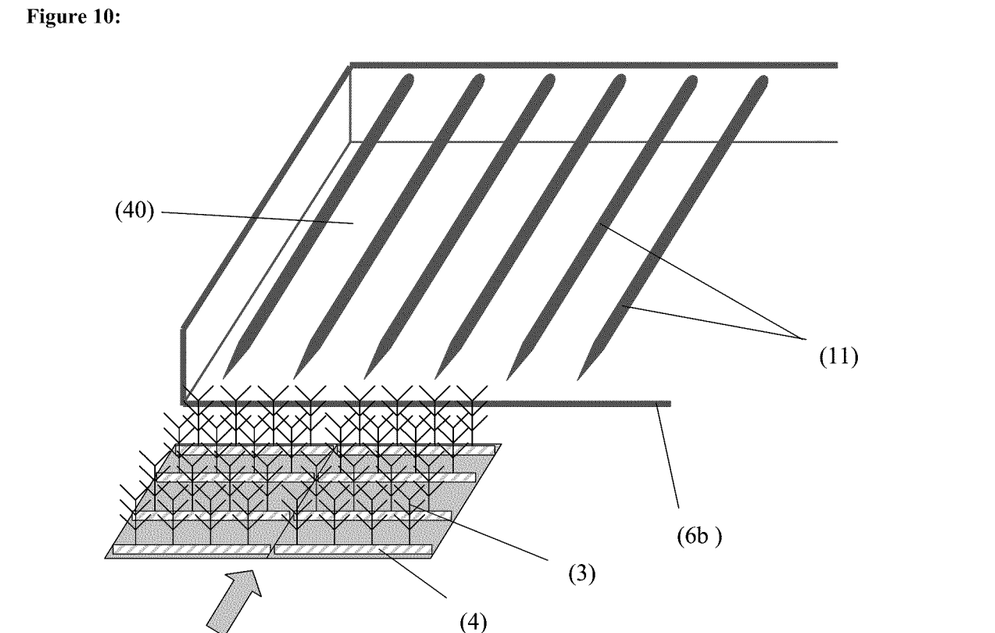

The at least one carriage or suspension trolley (6b) further comprise means (11) by which the at least one container (4) can reversibly be affixed to. This means can be conventional fastener systems such as clamps, braces, straps and the like. In a particularly preferred embodiment, means (11) comprise various pins (FIG. 10) The container (4) with the plants (3) are held on the carriage or suspension trolley (6b) by the pins (which are put directly above the container (4)) and the bottom (40) of the carriage or suspension trolley (6b). According to the invention, the term "affixed to" means not only solutions where the containers (4) are immobilized in every dimension but includes also those technical systems that immobilize the containers in certain directions (e.g. in three horizontal directions and two vertical directions as depicted in FIG. 10). The latter means are even preferred as they provide a convenient solution where closing and opening—such as known with fastener systems—is not required.

Figure 11:
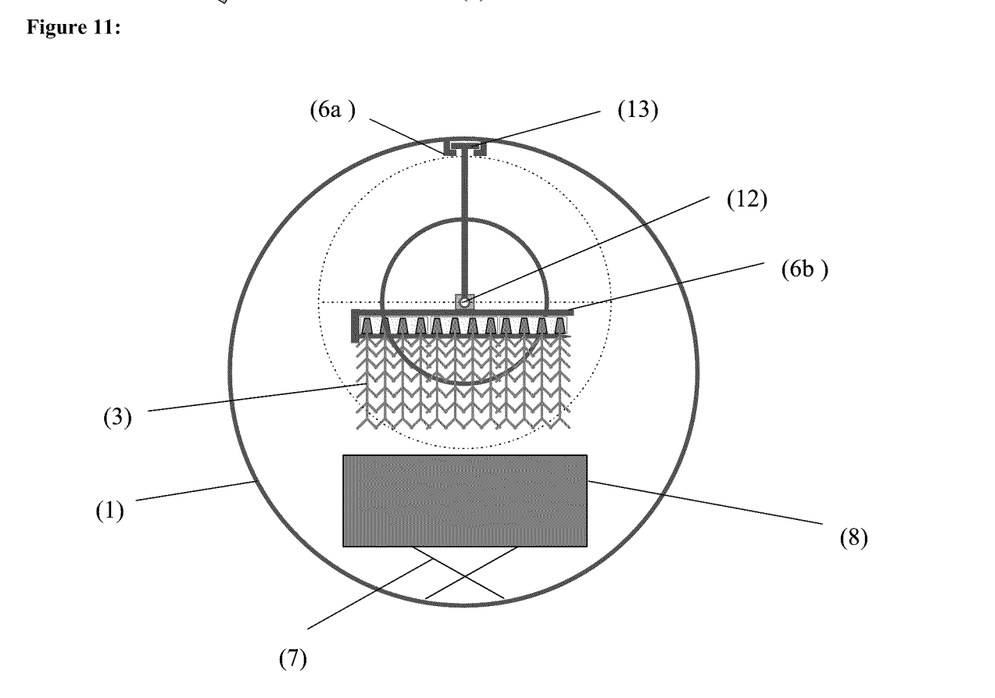
FIG. 11: Cross section of the turning of carriage or suspension trolley (6b) with the containers (4) within the enclosed chamber (1).

In addition, the at least one carriage or suspension trolley (6b) comprise means (12) by which the at least one container (4) can reversibly be turned. Such a mean can be a turning knuckle. Turning of the knuckle (and therefore the container (s) and the plant(s)) is electronically controlled via a computer system. Alternatively, a carriage or suspension trolley (6b) can also manually be turned. It can be particularly favorable that the dimensions of one carriage or suspension trolley (6b) are adapted to the dimensions of the enclosed chamber (1; see FIG. 9a, 9b, 11) for the reason that such a carriage or suspension trolley (6b) needs only to be turned twice (at the beginning and at the end of one vacuum cycle).

Figure 1A:
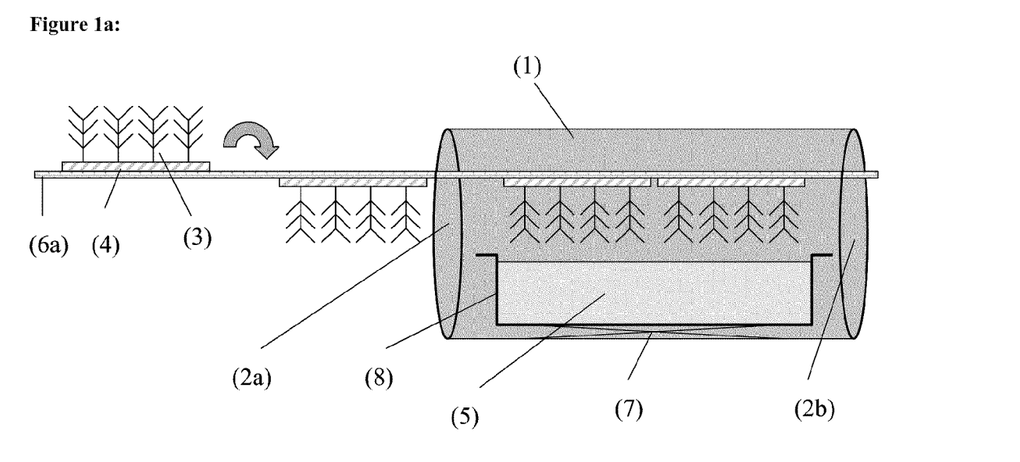
FIGS. 1a and 1b: An example of a mechanic and/or electric monorail system.
Figure 1B:
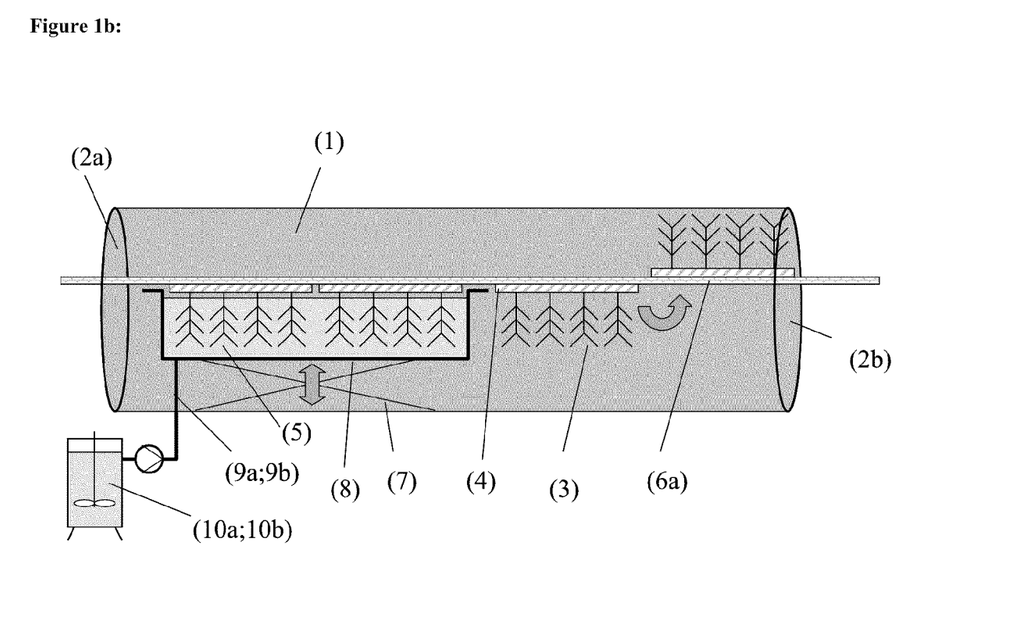
Figure 2A:
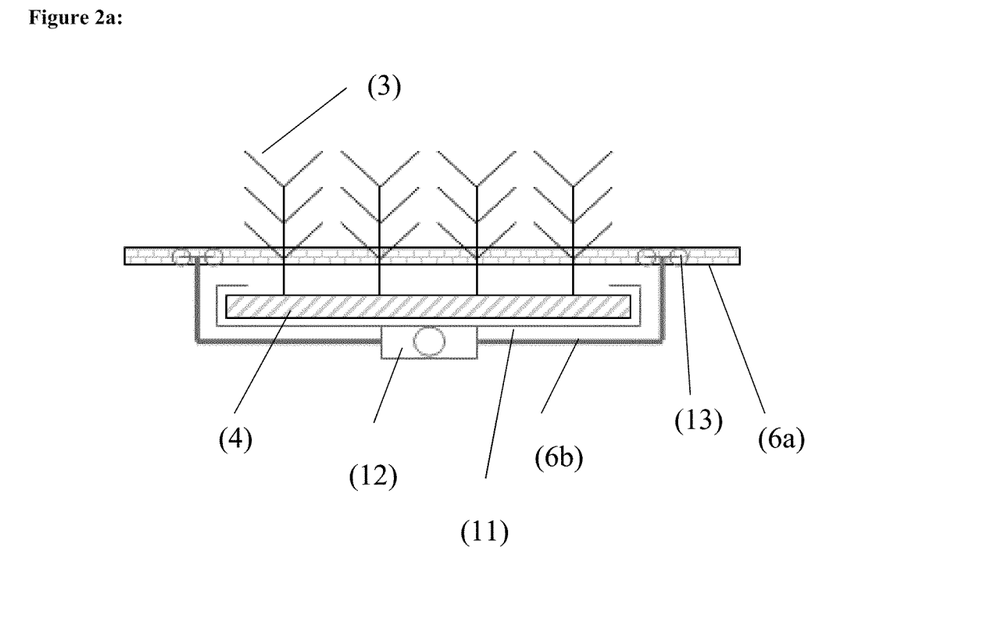
FIG. 2a: Side view of the one carriage or suspension trolley (6b) with the monorail system (6a) in conveying direction.
Figure 2B:
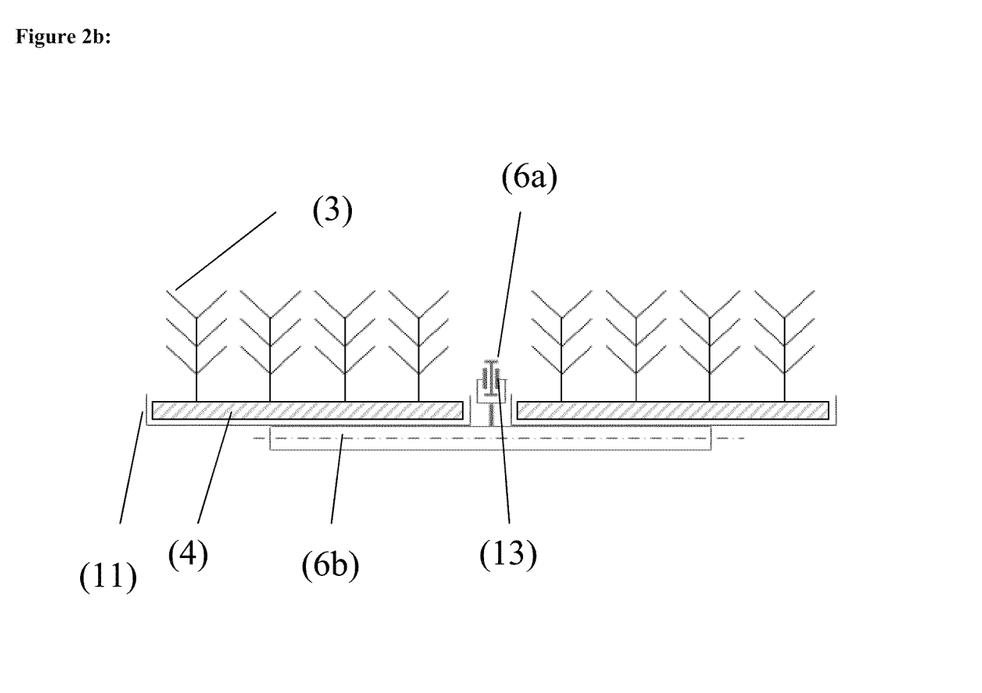
FIG. 2b: Side view of the one carriage or suspension trolley (6b) with the monorail system (6a) in monorail direction.
Figure 3:
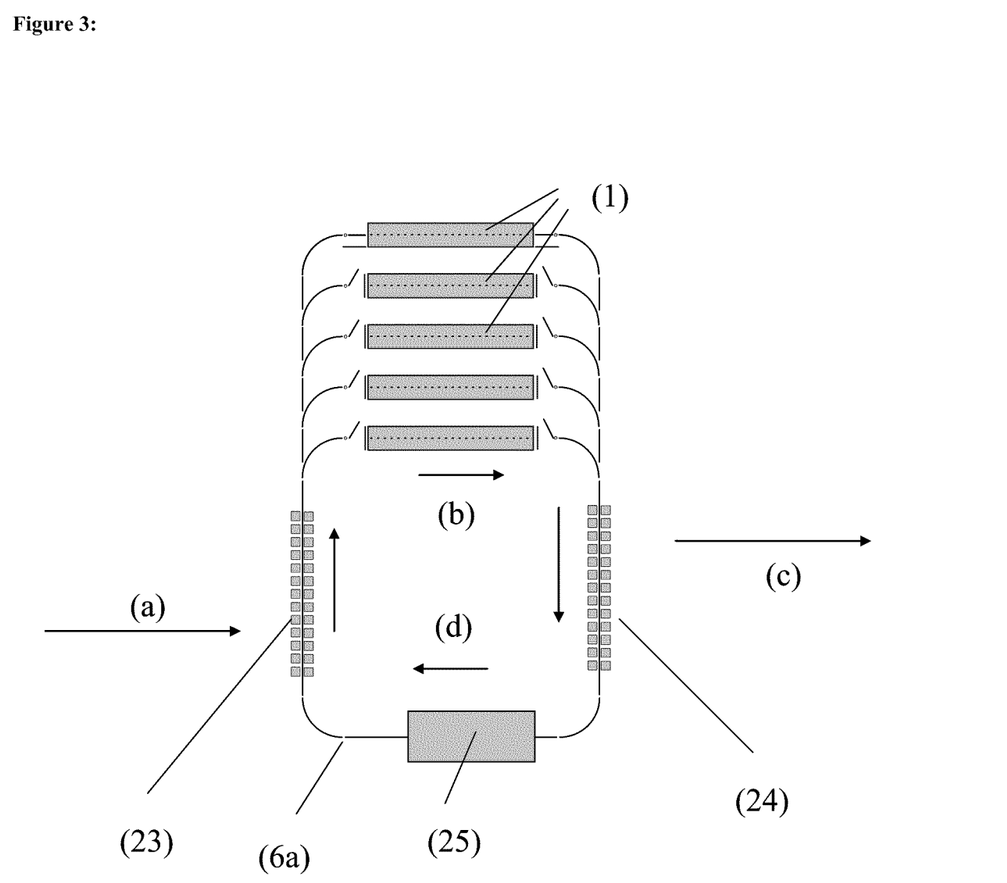
FIG. 3: Top view of an infiltration system with five enclosed chambers (1; autoclaves) and the enclosed rail system (6a). Arrow a) indicates that containers (4) with the plants are loaded onto the electric monorail. Containers (4) are transported via the enclosed chambers (1, arrow b)) to the unloading station (24, arrow c)). Arrow d) indicates that the monorail (with the carriage or suspension trolley 6b) is cleaned or disinfected afterwards.

In practice the conveying of the containers (4) is preferably realized by an electric monorail system with one or two containers (4) in each individual section (see FIGS. 2 and 3). Several sections are combined to a train-like unit that covers the area of one batch dipping. The monorail system allows a high throughput when considering separate loading (23) and unloading stations (24). Returning monorails systems are supposed to be cleaned in a cleaning and/or disinfection unit (25) before reuse to prevent unnecessary spreading of e.g. genetically modified material. The layout concept of such a system is shown in FIG. 3.

Another preferred embodiment of the invention comprises a system, wherein the technical transportation system comprises:
- at least one robot handling unit (20) to reversibly turn the at least one container (4) with the at least one plant (3) and to put it upside down on at least one frame (27),
- a rail system (28) for transporting the at least one frame (27) with the at least one plant (3) in the at least one container (4) on rolls (29) into and out of the at least one enclosed chamber (1).

In this system, at least one plant (3) in the at least one container (4) is transported, preferably via a roller conveyor (26), to at least one robot handling unit (20). The at least one robot handling unit (20) takes hold of the at least one container (4) and puts the container together with the plant(s) (3) upside down on at least one frame (27).

Figure 5A:
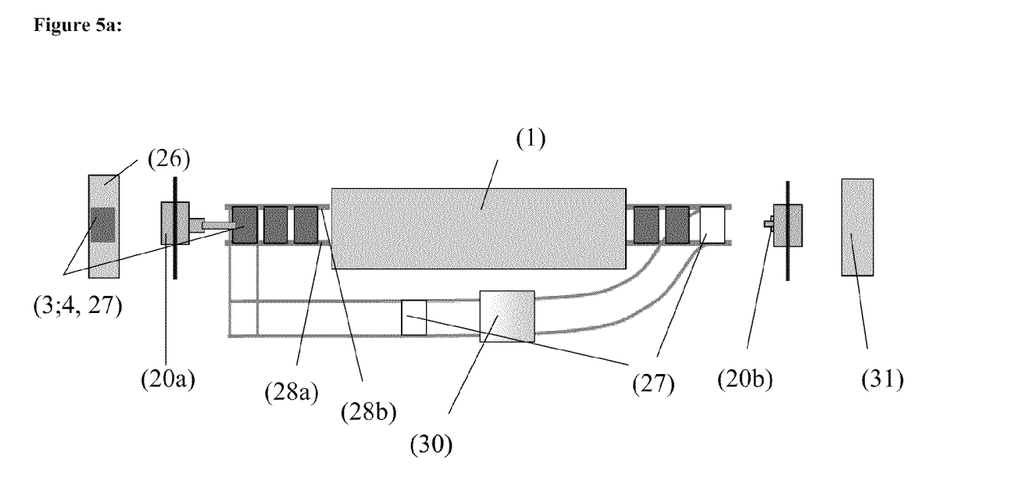
FIG. 5a: Top view of the infiltration system with at least two robot handling units (20).
Figure 5B:
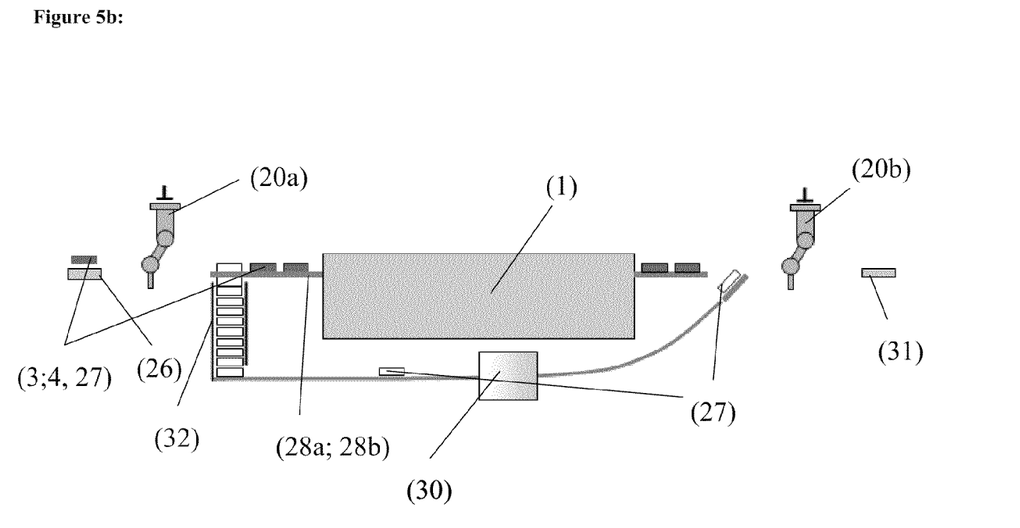
FIG. 5b: Side view of the infiltration system with at least two robot handling units (20).

The frame (27) is constructed to carry one container (4; preferably at the edges of the container). The frame (27) is preferably transported by at least two, preferably at least four, rolls (29) on a rail system (28), preferably a rail system with at least two rails (28a and 28b), into and out of the at least one enclosed chamber (1). The rolls (29) can either be mounted with the frames (27) or alternatively, they are part of the rail system itself. The containers on the frames (27) move into the enclosed chamber (1) when they are pushed by the following frames. This can be combined with sloping rails and a frame stacking device (32) with an engine to transport the frames back from a lower position to the starting position (see FIG. 5b). Alternatively a traction system in the loading section moves them into the at least one enclosed chamber (1). Other similar transportation means known to the skilled person in the art can also be used.

A particularly preferred embodiment of the invention relates to a system, wherein:
- the parts of the rail system that are located within the at least one enclosed chamber (1),
- the at least one frame (27), and
- the rolls (29), are made of thermoresistant materials such as for example steel (preferably stainless steel), plastic an the like.

Advantages of such system are that no movable parts are permanent inside the vacuum chamber (e.g. for the cleaning process) and that e.g. only simple steel rails are needed inside the chamber. The maintenance is thus simplified with only damaged frames (27) to be removed from the production line, while the vacuum chambers (1) can carry on working. The frames (27) used for the transport can be recirculated and cleaned automatically by a cleaning and/or disinfection unit (30).

In a preferred embodiment of the invention at least two robot handling units are used. In this embodiment one robot handling unit (20a) loads the containers (4) on the frames (27). The frames (27) are transported through a first closable opening (2a) into the enclosed chamber (1). After drawing vacuum, the containers (4) are transported out of the enclosed chamber (1) through a second closable opening (2b). The robot handling unit (20b) turns the containers upside up and puts them on a further roller conveyor (31) to transport them to the post-growth area.

According to the present invention, the term "reversibly turn the at least one container (4) upside down" means that the container (4) is rotated by more than 90 degrees (preferably about 180 degrees) in such a way that those parts above the soil (or substrate) of the plant are upside down. This rotation occurs preferably outside or in the enclosed chamber (1). The term further means that the at least one container (4) is again rotated back to its original position after the infiltration process took place. The second rotation is preferably completed within the enclosed chamber (1) but can also be done after the container (4) has been transported out of the enclosed chamber (1)

The infiltration system of the present invention further comprises means by which at least one part of the at least one plant (3) can be contacted with a suspension of infectious particles and/or microorganisms (5). The at least one part of the at least one plant (3) can be contacted with the suspension (5) either outside the enclosed chamber (1) or within it.

Means to contact the plant (3) outside the enclosed chamber (1) with the suspension (5) comprise for example at least one box (14) wherein the at least one plant (3) in at least one container (4) is put upside down into it; means (15) to reversibly close the box and an inlet pipe (9*a*) and a tank (10*a*) from which the suspension (5) is pumped into the closed box (14). Such a box (14) or several such boxes (14) can be loaded into the enclosed chamber (1). Alternatively, they are stacked into a cart (18) and the cart (18) is moved into the enclosed chamber (1) for example with a rail system as herein discussed. In another embodiment, the box is itself part of a cart that comprises wheels.

A preferred embodiment of the invention relates to a system, wherein the at least one enclosed chamber (1) comprises the means by which at least one part of the at least one plant (3) can be contacted with a suspension of infectious particles and/or microorganisms (5).

Within the enclosed chamber (1) such means can be for example means for dipping the plants into a basin (8) comprising a suspension (5). These can for example be realized by retractable mountings for the plant(s) (3) in the container(s) (4). These retractable mountings are preferably a part of a carriage or suspension trolley (6*a*).

In case of spray infiltration, the means can also be spray nozzles that are a part of the enclosed chamber (1). Such nozzles can for example be mounted in the wall of the enclosed chamber. The nozzles are connected to means preferably outside of the enclosed chamber (1) to supply the nozzles with the suspension (5; such as for example an inlet pipe 9*a* and a tank 10*a*). Pressure to spray the suspension on at least one part of the at least one plant (3) within the enclosed chamber (1) can be provided by conventional means such as motor driven pumps and the like.

A preferred embodiment of the present invention comprises a systems, wherein the means by which at least one part of the at least one plant (3) can be contacted with a suspension of infectious particles and/or microorganisms (5), comprises at least one open basin (8) comprising the suspension (5). Preferably the enclosed chamber (1) comprises means (7) to move the at least one basin (8) comprising the suspension (5) to contact the at least one part of the at least one plant (3) with the suspension (5) in the basin (8).

In a preferred embodiment of the invention the basin (8) is on top of the moving means (7) and the basin (8) is lifted by the moving means (7) in order to bring the basin (8) with the suspension (5) in contact with at least one part of the at least one plant (3). As the plant is preferably upside down in the enclosed chamber (1), the suspension (5) contacts those parts of the plants that are above the substrate (stem and leaves). In this embodiment of the invention, the moving mean (7) is preferably a hydraulic ramp.

In case the carriage or suspension trolley (6*b*) with the at least one container (4) is turned upside down within the enclosed chamber (1), the plants (3) can be dipped into the open basin (8) by the rotation movement directly. In such a preferred embodiment, no retractable mountings or moving means (7) are required.

Another preferred embodiment of the invention relates to a system, wherein the basin (8) comprising the suspension of infectious particles and/or microorganisms (5) further comprises at least one connection (9a; 9b) to means (10a; 10b) outside the enclosed chamber by which the suspension (5) can be removed and/or by which the basin (8) can be refilled with new suspension of infectious particles and/or microorganisms (5). In this embodiment, the suspension (5) is pumped into the basin (8) from a tank (10a) through an inlet pipe (9a). The suspension (5) is removed from the basin (8) by an outlet pipe (9b, which can be the same as the inlet pipe 9a or different) to a tank (10b which can be the same as the tank 10a or different). Before removing the suspension from the basin (8) it can optionally be inactivated by the disinfection means of the enclosed chamber (1). The preparation of the suspension (5) is preferably exchanged every other day or alternatively once a day. The suspension (5) is also exchanged when other infectious particles and/or microorganisms are infiltrated.

In a further preferred embodiment of the invention, the infiltration system further comprises disinfection means for disinfecting the suspension of infectious particles and/or microorganisms (5). When an autoclave is used, the enclosed chamber (1) can disinfect the suspension (5) via steam. Alternatively the system comprises means to chemically disinfect the suspension (5).

Figure 4:
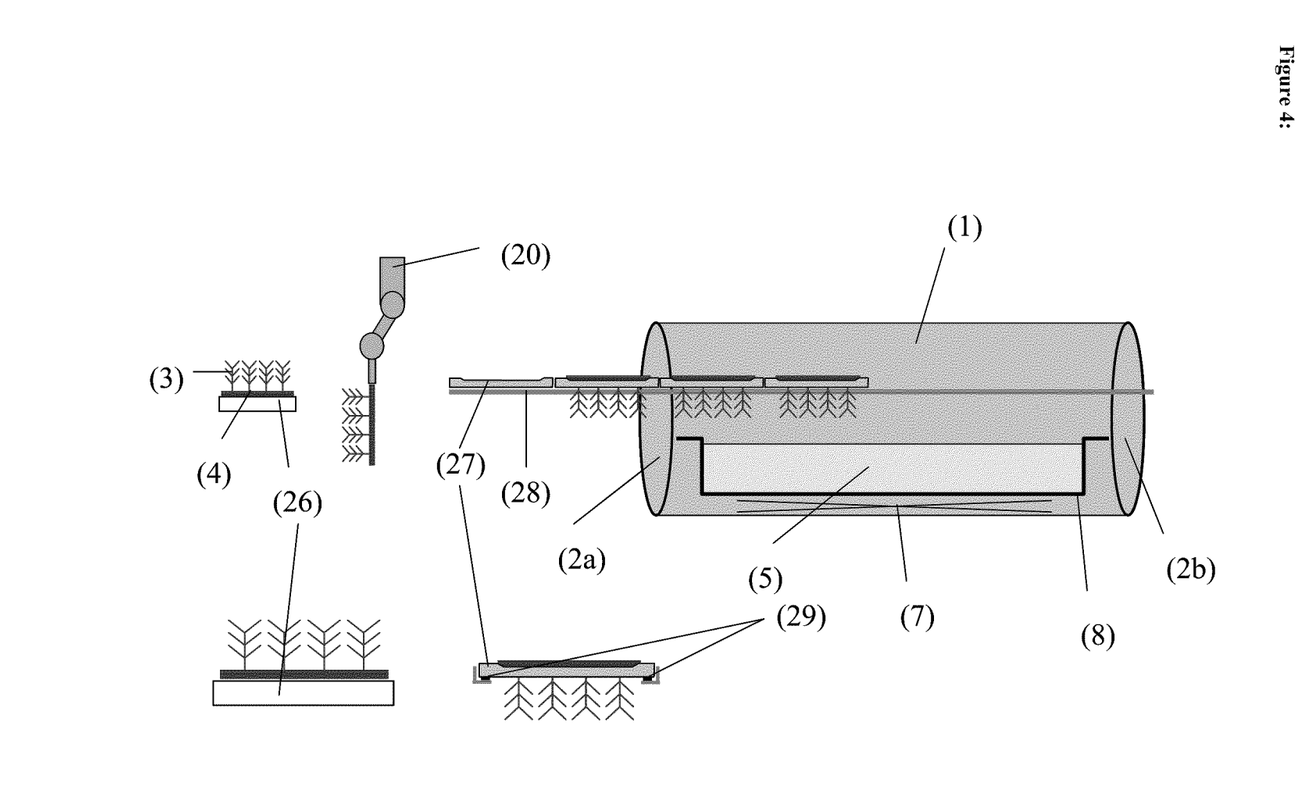
FIG. 4: An example of an infiltration system with at least one robot handling unit (20).

With an enclosed infiltration chamber (1) a batch wise infiltration is possible. By using more enclosed chambers (1) in parallel (see FIGS. 4 and 7) and in a delayed operation mode (FIG. 7), a continuous or quasi-continuous loading and unloading of the containers becomes possible.

In such a system, several enclosed chambers (1) in parallel are supplied via inlet pipes (9a) with the suspension comprising infectious particles and/or microorganisms (5) via one central preparation unit/tank (10a). The latter (10a) has access to potable water (33) and infectious particles and/or microorganisms (34) to prepare the suspension. The enclosed chambers (1) are supplied via a steam pipe (35) with steam to disinfect the suspension (5). The system further comprises an outlet pipe (9b) to transport the disinfected suspension (5) as waste to a corresponding waste bin. The (e.g. GMO containing) air exhaust is transported via pipe (36) to subsequent processing steps. The system also comprises a pipe system (37) with cooling water for the vacuum pump (39).

Figure 7:
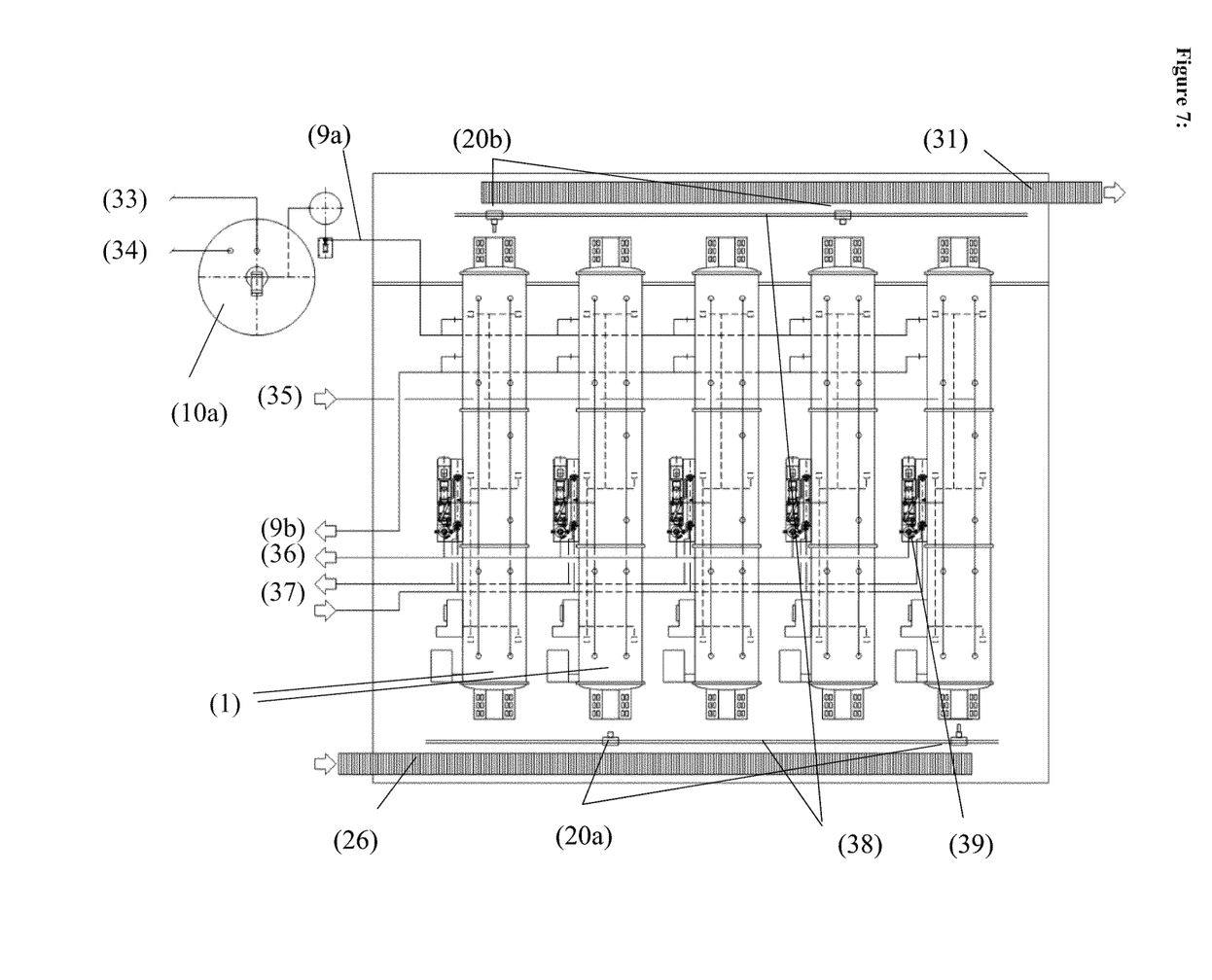
FIG. 7: Top view of an infiltration system with several enclosed chambers (1; autoclaves).

The delayed operation mode is shown in FIG. 7. While the two loading robot handling units (20a) are filling two enclosed chambers (1), the two unloading robot handling units (20b) are unloading two different enclosed chambers (1) where vacuum has already been drawn to. Thereby, a continuous operation mode can be put into practice.

The robot handling (20a; 20b) units are preferably moved to the different enclosed chambers (1) via another rail system (38). In such as system, an appropriately dimensioned waiting area for the containers (26) is required.

Figure 8A:
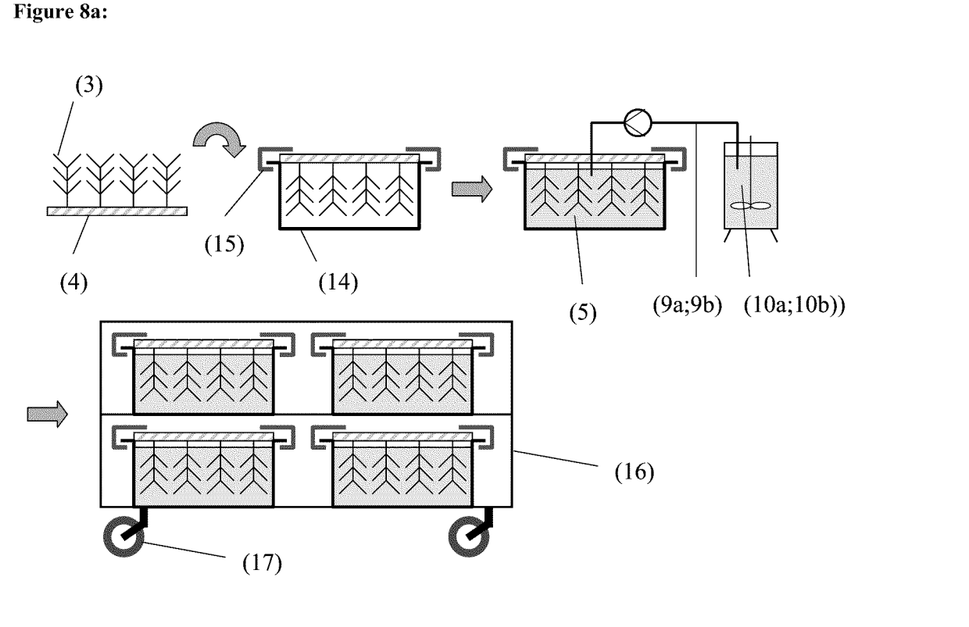
FIGS. 8a and 8b: An example of a single unit compartment infiltration system.
Figure 8B:
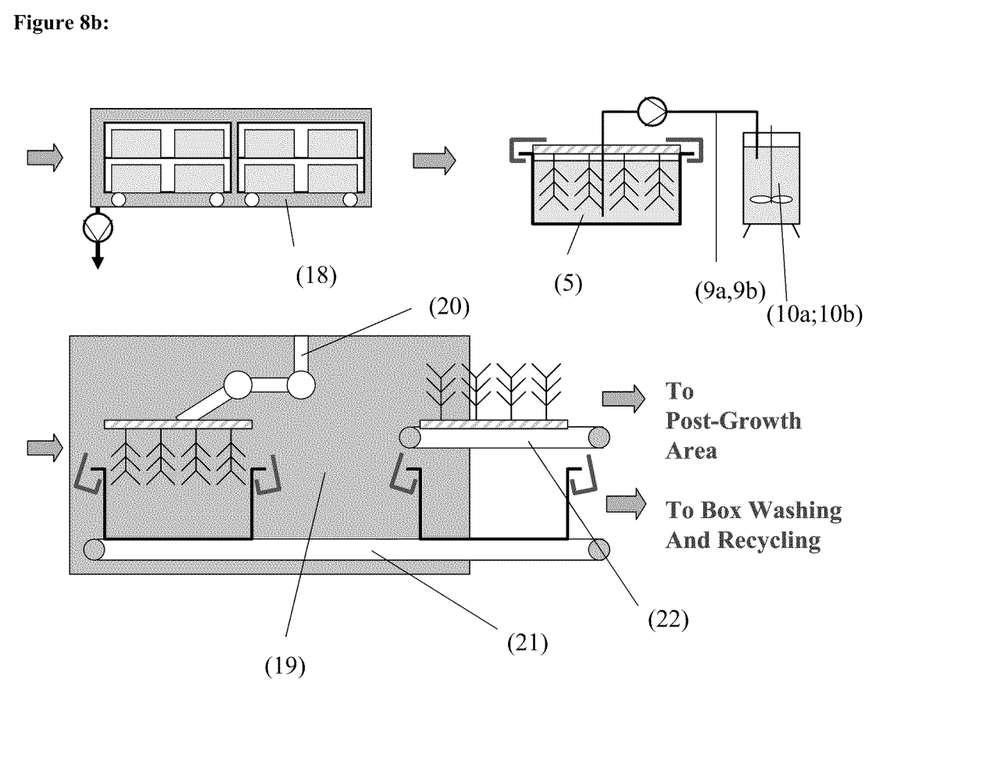

In another embodiment of the invention, all plants (3) of a batch are loaded into the vacuum chamber (1) together. This can for example be accomplished by stacked single units (see FIG. 8).

Such a system comprises as a technical transportation system at least one cart comprising:
  wheels, and
  means to transport at least one plant (3) on the at last one container (4) into and out of the at least one enclosed chamber (1).

The means to transport at least one plant (3) on the at least one container (4) into and out of the at least one enclosed chamber (1) is a frame where it is possible to affix the containers (4) reversibly. Such a frame may also comprise means by which the at least one container (4) is reversibly turned upside down. Alternatively, the container (4) is already affixed to the frame in such a manner (e.g. by a robot handling unit). In another embodiment the means to transport at least one plant (3) on the at least one container (4) into and out of the at least one enclosed chamber (1) is a box into which the containers (4) with the plants (3) can be put into (preferably upside down). The suspension comprising infectious particles and or microorganisms is filled into the cart (outside or inside the enclosed chamber (1)). In a preferred embodiment the cart comprises means to fill and remove the suspension (5; similar to 9a, 10a, 9b, 10b).

In case the cart comprises a frame, the plants (3) can also be dipped into an open basin (8) within the enclosed chamber (1). This can be done by moving means (7), retractable mountings (as part of the frame) or—in case the frame further comprises means to turn the at least one container (4) upside down—by a rotation movement.

Another embodiment of the present invention is therefore related to a system, wherein the technical transportation system comprises:
  at least one box (14) to place at least one plant (3) in at least one container (4) upside down into the box (14),
  means (15) to reversibly close the box (14),
  least one cart (16) to stack at least one box (14) (and preferably to stack at least more than one box (14)),
  and wherein the means by which at least one part of the at least one plant (3) is contacted with a suspension of infectious particles and/or microorganisms (5) further comprise:
  means (9a, 10a) to fill the box (14) with a suspension of infectious particles and/or microorganisms (5),
  means (9a or 9b, 10a or 10b) by which a suspension of infectious particles and/or microorganisms (5) can be removed from the box (14).

In this embodiment of the invention, at least one plant (3)—and preferably more than one plant—in at least one container (4) is placed upside down on a box (14) and is fixed there by fixation means (15) such as e.g. with clamps, braces, straps and the like. The box can be of any shape. However, a rectangular shape is preferred.

The box (14) is filled with the suspension (5) from a tank (10a) via an inlet pipe (9a) and optionally stacked with other boxes into a cart (16).

In an another embodiment, the boxes (14) are filled with the suspension (5) after they have been put into a cart (16). This can be done through various inlet pipes (9a; for example for every box). For such an embodiment, the cart has to be adapted accordingly. Alternatively, the boxes (14) are connected with each other by connecting means (e.g. pipes) and the suspension (5) is filled through one (or a few) inlet pipe(s) and is distributed via the connecting means between the boxes (14).

The cart has an opening to take up the boxes (14). The cart can be of any shape. However, a rectangular shape is preferred.

The cart preferably accommodates several boxes on different levels and travels on wheels (17) or other conventional transportation means into the enclosed chamber (1 and 18 in FIG. 8). The latter is preferably a vacuum chamber comprising at least one closable opening (2). An optional rail system to drive the carts (16) in and out of the enclosed chamber (1 and 18) simplifies the loading and unloading process.

After the carts (16) are put into the enclosed chamber (1 and 18), the chamber is closed and the vacuum applied. After release of the vacuum, the carts (16) are taken out from the enclosed chamber (1 and 18). The suspension (5) is pumped out of the boxes (14) again by an outlet pipe (9b, which can be the same as the inlet pipe 9a or different) to a tank (10b which can be the same as the tank 10a or different).

The plants (3) are removed now from the boxes (14) after the boxes (14) are unclamped (or opened by other means). This is preferably done in a separate (enclosed) wet area (19) wherein the boxes (14) are optionally put on a transportation belt (21). The plants (3) in the containers (4) are turned, preferably via an robot handling unit (20), and brought to the post-growth area (e.g. via a belt (22)). The boxes (14) are washed and recycled.

In a preferred embodiment of the invention, the boxes (14) do further comprise a sterile filter to avoid that air exhaust (e.g. aerosols comprising suspension of infectious particles and/or microorganisms) leaks from the boxes (14).

In all these embodiments of the invention the units and/or containers are preferably connected to the moving framework for a better coupling. Monorail systems, actuators, robots, manipulators and the like can be engaged with the framework. In addition, the units and/or containers preferably comprise means to avoid falling off the substrate during the rotation process. These means can be for example grids, films, filter, canvas and the like.

The present invention also relates to methods for the infiltration of a suspension of infectious particles and/or microorganisms (5) into at least one plant (3) comprising the use of a system or systems as described herein.

A further embodiment of the invention is the use of a system or systems as described herein for the large-scale infiltration of plants (3).

In a preferred embodiment the system(s) and method(s) of the present invention are used for large-scale infiltration of plants such as for example for an amount of 10 to 1000 m² plants per hour.

BRIEF DESCRIPTION OF THE DRAWINGS

FIG. 10: Carriage or suspension trolley (6b) comprising means (11) by which the at least one container (4) can reversibly be affixed to.

EXAMPLE

The production of a monoclonal antibody is usually based on mammalian cell culture fermentation in large fermenter vessels. Here, a typical industrial batch size is 1 kg of protein. It can be beneficial to produce this pharmaceutical product with a plant based technology, as plants have for example the benefit not to be able to be a host for viruses that are pathogenic to humans. Therefore, the potential risk for a contaminated pharmaceutical product is reduced significantly.

To produce an antibody in a plant a transient genetically modification of the plant *Nicotiana Benthamiana* by a vacuum infiltration method can be used. Using this method, the yield of antibody per square meter of plants is typically 1 g. In consequence an area of 1.000 square meters is necessary per batch of 1 kg protein.

A vacuum infiltration of such an acreage using technology of the state of the art (like described in WO 01/12828 A) will lead to large and in practice unrealistic process times. The state of the art method is manual and therefore limited in size of the plant area handled at a time. The maximum for a single person is one tray of plants. Typically a tray for *Nicotiana benthamiana* has a size ⅙th square meter. Therefore 12.000 single handling steps (loading and unloading of 6.000 trays) are necessary. The introduction and removal of the plants upside down into the infiltration solution has to be done very carefully and will take at least 1 Minutes each manipulation. Therefore, the time for manipulation alone will be 200 hours. As vacuum chambers with manual load and unload can only be handled up to the size of one square meter an additional process time for 1.000 vacuum cycles of at least 5 minutes have to be added. In combination, the complete process takes more than 280 hours, which is more than 11 days.

Using an automated loading procedure, e.g. an electric rail system according to the current invention, the loading of large vacuum chambers can be realized. For a chamber usable for 20 square meter plant area the loading and unloading procedure takes about 5 minutes each. In such a large vacuum chamber, the vacuum cycle will take longer as larger volumes have to be evacuated. One vacuum cycle will take 10 min instead of 5. This way the processing of 20 square meter takes 20 minutes and the complete large batch is processed in less than 17 hours. In consequence, using the invention of the current application, the performance is increased by a factor of 17. And surprisingly, the effectivity of the loading and unloading means of the invention even overcompensates the longer time for the actual vacuum cycle of a large scale vacuum chamber. This way it is possible to process industrial size batches in process times which can be met in realistic conditions for pharmaceutical production.

The invention claimed is:

1. A system for the infiltration of a suspension of infectious particles and/or microorganisms into at least one plant comprising:

a) at least one enclosed vacuum chamber comprising:

at least one closable opening through which the at least one plant in at least one container is transported into and out of the at least one enclosed chamber by a technical transportation system, b) the technical transportation system to transport the at least one plant in at least one container into and out of the at least one enclosed chamber, and c) at least one box or open basin configured to contact at least one part of the at least one plant with a suspension of infectious particles and/or microorganisms, wherein the technical transportation system comprises at least one mechanic and/or electric rail system and optionally at least one robot handling unit to transport the at least one plant in at least one container into and out of the at least one enclosed chamber, wherein the at least one mechanic and/or electric rail system comprises at least one rail and at least one carriage or suspension trolley to transport at least one container into and out of the at least one enclosed chamber, wherein the at least one carriage or suspension trolley is mounted within the at least one rail with at least one coupling, wherein the at least one carriage or suspension trolley further comprises a fastener system to reversibly affix the at least one container and a turning knuckle capable of reversibly turning the at least one container upside down.

2. The system according to claim 1, wherein the at least one enclosed chamber comprises the at least one open basin comprising the suspension of infectious particles and/or microorganisms.

3. The system according to claim 2, wherein the enclosed chamber comprises means to move the at least one open basin comprising the suspension of infectious particles and/or microorganisms to contact the at least one part of the at least one plant with the suspension in the open basin.

4. The system according to claim 2, wherein the open basin comprising the suspension of infectious particles and/or microorganisms further comprises at least one connection to means outside the at least one enclosed chamber configured to remove the suspension and configured to refill the open basin with a new suspension of infectious particles and/or microorganisms.

5. The system according to claim 1, wherein the system further comprises an autoclave to disinfect the suspension of infectious particles and/or microorganisms.

6. The system according to claim 1, wherein the technical transportation system comprises at least one cart comprising:
   wheels, and
   a frame to transport at least one plant in the at last one container into and out of the at least one enclosed chamber.

7. The system according to claim 1, further comprising an inlet pipe and a tank configured to fill the at least one box with a suspension of infectious particles and/or microorganisms and to remove a suspension of infectious particles and/or microorganisms from the box, wherein the technical transportation system comprises:
   the at least one box to place at least one plant in at least one container upside down into the at least one box,
   a fastener system to reversibly close the at least one box,
   at least one cart to stack the at least one box.

8. The system according to claim 1, wherein the turning knuckle is configured to turn the at least one container upside down to contact at least one part of the at least one plant with the suspension in the at least one open basin.

9. The system according to claim 1, wherein the turning knuckle is configured to turn the at least one container upside down before the at least one plant is transported into the at least one enclosed chamber, and wherein the turning knuckle is configured to turn the at least one container right side up before the at least one plant is transported out of the at least one enclosed chamber.

10. The system according to claim 1, wherein the at least one enclosed vacuum chamber comprises a vacuum providing means to apply a vacuum to said chamber.

11. The system according to claim 10, wherein the vacuum providing means is a vacuum pump.

* * * * *

UNITED STATES PATENT AND TRADEMARK OFFICE
CERTIFICATE OF CORRECTION

| | | |
|---|---|---|
| PATENT NO. | : 8,614,088 B2 | Page 1 of 1 |
| APPLICATION NO. | : 12/863933 | |
| DATED | : December 24, 2013 | |
| INVENTOR(S) | : Dujardin et al. | |

It is certified that error appears in the above-identified patent and that said Letters Patent is hereby corrected as shown below:

On the title page item (73), should read:

Icon Genetics GmbH, Halle (DE)

Signed and Sealed this
Third Day of June, 2014

Michelle K. Lee
*Deputy Director of the United States Patent and Trademark Office*